(12) United States Patent
Knust et al.

(10) Patent No.: US 7,932,269 B2
(45) Date of Patent: Apr. 26, 2011

(54) SULFONAMIDES AS OREXIN ANTAGONISTS

(75) Inventors: Henner Knust, Rheinfelden (DE); Matthias Nettekoven, Grenzach-Wyhien (DE); Emmanuel Pinard, Linsdorf (FR); Olivier Roche, Folgensbourg (FR); Mark Rogers-Evans, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 291 days.

(21) Appl. No.: 12/353,506

(22) Filed: Jan. 14, 2009

(65) Prior Publication Data
US 2009/0186920 A1 Jul. 23, 2009

(30) Foreign Application Priority Data

Jan. 21, 2008 (EP) .................................... 08150435

(51) Int. Cl.
*A61K 31/451* (2006.01)
*A61K 31/40* (2006.01)
*C07D 295/192* (2006.01)
*C07D 211/30* (2006.01)

(52) U.S. Cl. ......... 514/330; 514/423; 546/226; 548/540

(58) Field of Classification Search .................. None
See application file for complete search history.

(56) References Cited

U.S. PATENT DOCUMENTS 7,312,358 B2 * 12/2007 Quattropani et al. ........... 564/80
2007/0185136 A1 8/2007 Courtemanche

FOREIGN PATENT DOCUMENTS
WO WO 02/32864 4/2002

OTHER PUBLICATIONS

Siegel, Annu. Rev. Psychol. vol. 55, pp. 125-148 (2004).
De Lecea et al., Proc. Natl. Acad. Sci. USA vol. 95 pp. 322-327 (1998).
Sakurai et al., Cell vol. 92 pp. 573-585 (1998).
Sakurai, T., Regulatory Peptides vol. 126 pp. 3-10 (2005).
Peyron et al., J. Neurosci. vol. 18 pp. 9996-10015 (1998).
Nambu et al., Brain Res. vol. 827 pp. 243-260 (1999).
Chemelli et al., Cell, vol. 98 pp. 437-451 (1999).
Lin et al., Cell, vol. 98 pp. 365-376 (1999).
Nishino et al., Lancet vol. 355 pp. 39-40 (2000).
Peyron et al., Nature Medicine vol. 6 pp. 991-997 (2000).
Mignot et al., Sleep vol. 11, pp. 1012-1020 (1997).
Piper et al., Eur. J. Neuroscience vol. 12 pp.726-730 (2000).
Sakamoto et al., Regul. Pept. vol. 118 pp. 183-191 (2004).
Ida et al., Biochem. Biophys. Res. Comm. vol. 270 pp. 318-323 (2000).
Kuru at al., Neuroreport vol. 11 pp. 1977-1980 (2000).
Winsky-Sommerer et al., J. Neuroscience vol. 24 pp. 11439-11448 (2004).
Chang et al., Neurosci. Res. pp. 356-362 (2006).
Suzuki et al., Brain Research vol. 1044 pp. 116-121 (2005).
Digby et al., J. Endocrinol. vol. 191 pp. 129-136 (2006).
Cai at al., Expert Opin. Ther. Patents vol. 16(5) pp. 631-646 (2006).
Bingham et al., Current Opinion in Drug Discovery & Development vol. 9(5) pp. 551-559 (2006).
Bourgin et al., J. Neurosci. vol. 20(20) pp. 7760-7765 (2000).
Smith et al.,Neurosci. Lett vol. 341(3) pp. 256-258 (2003).
Quattropani et al., Journal of Medicinal Chemistry vol. 48(24) pp. 7882-7905 (2005).
Malherbe et al., Mol. Pharmacol. vol. 64 pp. 823-832 (2003).
Yang et al, *Bioorganic & Medicinal Chemistry Letters*, (2008) 1340-1345 18:4 XP022479328.
Database Beilstein, XP002525000 Accessin No. 9336940, 2009.
Aissaoui H et al, *Bioroganic & Medicianl Chemistry Letters*, (2008) XP025562032, 18:21, 5729-5733.

\* cited by examiner

*Primary Examiner* — Kamal A Saeed
(74) *Attorney, Agent, or Firm* — George W. Johnston; Patricia S. Rocha-Tramaloni; Kimberly J. Prior

(57) ABSTRACT

The present invention is concerned with novel sulfonamides of formula

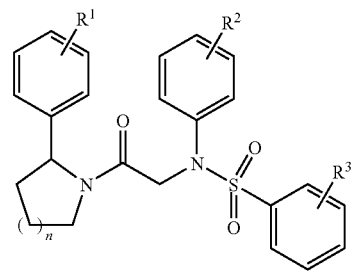

wherein $R^1$, $R^2$, $R^3$ and n are as described in the description and claims. The compounds are orexin receptor antagonists, useful in the treatment of disorders, in which orexin pathways are involved.

9 Claims, No Drawings

SULFONAMIDES AS OREXIN ANTAGONISTS

PRIORITY TO RELATED APPLICATION(S)

This application claims the benefit of European Patent Application No. 08150435.9, filed Jan. 21, 2008, which is hereby incorporated by reference in its entirety.

BACKGROUND OF THE INVENTION

Orexins (hypocretins), a family of hypothalamic neuropeptides, play an important role in modulating feeding behavior, energy homeostasis and the sleep-wake cycle (Siegel, *Annu. Rev. Psychol.*, 55, 125-148, 2004). The orexin-A/hypocretin1 (OX-A, 33 amino acids) and orexin-B/hypocretin2 (OX-B, 28 amino acids) are derived from the same precursor by proteolytic processing of 130 amino acids prepro-orexin (de Lecea et al., *Proc Natl Acad Sci USA*, 95, 322-327, 1998; Sakurai T. et al., *Cell*, 92, 573-585, 1998). The orexin levels show a diurnal variation being highest during the active cycle. Two receptor subtypes termed orexin-1 receptor ($OX_1R$) and orexin-2 receptor ($OX_2R$) have been identified. The characterization of both receptors in binding and functional assays demonstrated that $OX_2R$ is a non-selective receptor for both OX-A and —B, whereas $OX_1R$ is selective for OX-A, conversely OX-A is a non-selective neuropeptide and binds with similar affinities to $OX_1R$ and $OX_2R$, while OX—B is selective and has a higher affinity for OX2R (Sakurai T. et al., *Cell*, 92, 573-585, 1998). Both receptors belong to the class A family of G-protein-coupled receptors (GPCRs) that couple via $G_{q/11}$ to the activation of phospholipase C leading to phosphoinositide (PI) hydrolysis and elevation of intracellular $Ca^{2+}$ levels. However, it has been shown that OX2R could also couple via $G_{i/o}$ to cAMP pathway (Sakurai, *Regulatory Peptides*, 126, 3-10, 2005). Northern bloit analysis of adult rat tissues showed that the prepro-orexin mRNA is detected exclusively in the brain (except for a small amount in the testis) and that the $OX_1R$ and $OX_2R$ transcripts are also exclusively detected in the brain (Sakurai T. et al., *Cell*, 92, 573-585, 1998). Similar results were obtained using human multiple tissue Northern blot. Distribution studies in rat brain using in situ hybridization and immunohistochemistry have shown that orexin neurons are found only in the lateral hypothalamic area with their projections to the entire CNS (Peyron et al., *J Neurosci*, 18, 9996-10015, 1998; Nambu et al., *Brain Res.*, 827, 243-60, 1999). In addition, both $OX_1$ and $OX_2$ receptors are present in brain regions important for the regulation of sleep/wakefulness.

A disrupted orexin system is suggested to be the cause of narcolepsy based on following lines of evidence: (a) Prepro-orexin knockout mice possessed a phenotype with characteristics remarkably similar to narcolepsy (Chemelli et al., *Cell*, 98, 437-451, 1999), (b) a mutation (canarc-1), which disrupts the gene encoding $OX_2R$, was found to be responsible for canine narcolepsy (Lin et al., *Cell*, 98, 365-376, 1999), (c) lack of OX-A and OX—B was observed in human narcoleptic patients (Nishino et al., *Lancet*, 355, 39-40, 2000; Peyron et al., *Nature Medicine*, 6, 991-997, 2000), (d) it has been shown that Modafinil, an anti-narcoleptic drug with unknown mechanism of action, activates orexin neurons (Mignot et at., *Sleep*, 11, 1012-1020, 1997; Chemelli et al., *Cell*, 98, 437-451, 1999). The intracerebroventrictular (icv) administration of OX-A dose-dependently increases wakefulness in rat and also reduces total REM sleep by 84% (Piper et al., *Eur. J. Neuroscience*, 12, 726-730, 2000). Taken together, these observations are consistent with a crucial role of the orexin system in the modulation of sleep/wake cycle.

Orexin plays an important role in stress and anxiety via its interaction with the corticotropin-releasing factor (CRF) system in hypothalamus (Sakamoto et al., *Regul Pept.*, 118, 183-91, 2004). The icv injection of OX-A induces grooming (stress-response) which is blocked in part by a CRF antagonist (Ida et al., *Biochem. Biophys. Res. Comm.*, 270, 318-323, 2000). $OX_2R$ is highly expressed in adrenal medulla, whereas $OX_1R$ is high in adrenal cortex. Both OX-A and OX—B stimulate curticosterone release in plasma and induce c-Fos in paraventricular nucleus (PVN) in the hypothalamus (Kuru et al., *Neuroreport*, 11, 1977-1980, 2000). Furthermore, orexin neurons projecting to CRF neurons express mainly the $OX_2R$ (Winsky-Sommerer et al., *J. Neuroscience*, 24, 11439-11448, 2004). Therefore, OX2R stimulation activates the hypothalamo-pituitary-adrenal (HPA) axis. Interestingly, in this context, the orexin A-induced increases in plasma ACTH has been reported to be attenuated by a selective antagonist to OX-2R (N-{(1S)-1-(6,7-dimethoxy-3,4-dihydro-2(1H)-isoquinolinyl)carbonyl}-2,2-dimethylpropyl)-N-{4-pyridinylmethyl}amine (Chang et al., *Neurosci Res.*, 21 Dec. 2006). A recent predinical report (Suzuki et al., *Brain Research*, 1044, 116-121, 2005) has suggested an anxiogenic effect of OX-A. The icy injection of OX-A caused an anxiety-like behavior in mice. Effects were similar to those of corticotropin-releasing factor (CRF) that was tested at the same time for comparison. A recent study has also demonstrated the presence of functional OX1 and OX2 receptors in human adipose tissue and their roles in adipose tissue metabolism and adipogenesis (Digby et al., *J. Endocrinol.*, 191, 129-36, 2006).

In summary, considering the very diverse functions played by orexin system in arousal, sleep/wakefulness, appetite regulation and their roles in anxiety and stress response, etc., one expects that the drugs (or compounds) targeting orexin system will have beneficial therapeutic effects for the treatments of diseases like sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

Numerous documents describe the current knowledge on orexin pathway, for example the following documents:

Expert Opin. Ther. Patents (2006), 16(5), 631-646
  Current Opinion in Drug Discovery & Development, 2006, 9(5), 551-559
J. Neurosci (2000), 20(20), 7760-7765
Neurosci Lett, (2003), 341(3), 256-258

SUMMARY OF THE INVENTION

The present invention relates to compounds of formula I

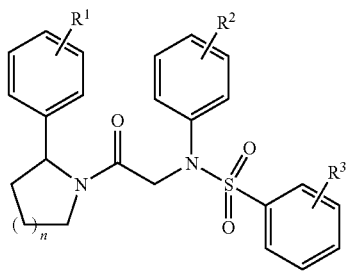

wherein
R¹, R² and R³ are each independently hydrogen, halogen, cyano, lower alky, lower alkoxy, lower alkyl substituted by halogen of lower alkoxy substituted by halogen, and
n is 1 or 2,
or to pharmaceutically suitable acid addition salts, optically pure enantiomers, racemates or diastereomeric mixtures thereof.

The invention also provides pharmaceutical compositions comprising a compound of formula I or a pharmaceutically suitable acid addition salt thereof and a pharmaceutically acceptable carrier. The invention further provides methods for the manufacture of compounds and compositions of the invention.

Compounds of formula I are orexin receptor antagonists and the related compounds may be useful in the treatment of disorders in which orexin pathways are involved; like sleep disorders including sleep apnea, narcolepsy, insomnia, parasomnia, jet lag syndrome, circadian rhythms disorder, and restless leg syndrome; psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and allodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

DETAILED DESCRIPTION OF THE INVENTION

The following definitions of the general terms used in the present description apply irrespective of whether the terms in question appear alone or in combination.

As used herein, the term "lower alkyl" denotes a straight- or branched-chain hydrocarbon group containing from 1-7 carbon atoms, for example, methyl, ethyl, propyl, isopropyl, n-butyl, i-butyl, t-butyl and the like. Preferred lower alkyl groups are groups with 1-4 carbon atoms.

The term "lower alkyl substituted by halogen" denotes an alkyl group as defined above, wherein at least one hydrogen atom is replaced by halogen, for example —$CF_3$, —$CHF_2$, —$CH_2F$, —$CH_2CF_3$, —$CH_2CH_2CF_3$, —$CH_2CF_2CF_3$ and the like. Preferred lower alkyl substituted by halogen groups are groups having 1-4 carbon atoms.

The term "lower alkoxy" denotes a group wherein the alkyl residue is as defined above and which is attached via all oxygen atom, for example, methoxy, ethoxy, propoxy, isopropoxy, n-butoxy, i-butoxy, 2-butoxy, t-butoxy and the like. Preferred alkoxy groups are groups with 1-4 carbon atoms.

The term "lower alkoxy substituted by halogen" denotes an alkoxy group as defined above wherein at least one hydrogen atom is replaced by halogen. Preferred lower alkoxy substituted by halogen groups are groups having 1-4 carbon atoms.

The term "halogen" denotes chlorine, iodine) fluorine and bromine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

Preferred compounds of formula I are those wherein n is 1.

Preferred compounds from this group are those, wherein R¹ is hydrogen and R² and R³ are as defined as above, for example the following compounds N-(4-chloro-phenyl)-3-methoxy-N-[2-oxo-2-(2-phenyl-pyrrolidin-1-yl)-ethyl]-benzenesulfonamide;
N-(4-chloro-phenyl)-4-methoxy-N-[2-oxo-2-(2-phenyl-pyrrolidin-1-yl)-ethyl]-benzenesulfonamide;
N-(4-chloro-phenyl)-2-methyl-N-[2-oxo-2-(2-phenyl-pyrrolidin-1-yl)-ethyl]-benzenesulfonamide;
3-chloro-N-(4-chloro-phenyl)-N-[2-oxo-2-(2-phenyl-pyrrolidin-1-yl)-ethyl]-benzenesulfonamide;
N-(4-chloro-phenyl)-4-methyl-N-[2-oxo-2-(2-phenyl-pyrrolidin-1-yl)-ethyl]-benzenesulfonamide;
N-(4-chloro-phenyl)-4-methoxy-N-[2-oxo-2-(2-phenyl-pyrrolidin-1-yl)-ethyl]-benzenesulfonamide;
4-chloro-N-(4-chloro-phenyl)-N-[2-oxo-2-(2-phenyl-pyrrolidin-1-yl)-ethyl]-benzenesulfonamide;
N-(4-chloro-phenyl)-4-fluoro-N-[2-oxo-2-(2-phenyl-pyrrolidin-1-yl)-ethyl]-benzenesulfonamide;
N-(4-chloro-phenyl)-3-fluoro-N-[2-oxo-2-(2-phenyl-pyrrolidin-1-yl)-ethyl]-benzenesulfonamide;
2-chloro-N-(4-chloro-phenyl)-N-[2-oxo-2-(2-phenyl-pyrrolidin-1-yl )-ethyl]-benzenesulfonamide;
2-chloro-N-(4-chloro-phenyl)-N-[2-oxo-2-(2-phenyl-pyrrolidin-1-yl)-ethyl]-benzenesulfonamide;
N-(4-chloro-phenyl)-2-fluoro-N-[2-oxo-2-(2-phenyl-pyrrolidin-1-yl)-ethyl]-benzenesulfonamide;
4-methoxy-N-(4-methoxy-phenyl)-N-[2-oxo-2-(2-phenyl-pyrrolidin-1-yl)-ethyl]-benzenesulfonamide;
N-(3-fluoro-phenyl)-4-methoxy-N-[2-oxo-2-(2-phenyl-pyrrolidin-1-yl)-ethyl]-benzenesulfonamide;
N-(4-fluoro-phenyl)-4-methoxy-N-[2-oxo-2-(2-phenyl-pyrrolidin-1-yl)-ethyl]-benzenesulfonamide;

4-methoxy-N-(2-methoxy-phenyl)-N-[2-oxo-2-(2-phenyl-pyrrolidin-1-yl)-ethyl]-benzenesulfonamide;

4-methoxy-N-[2-oxo-2-(2-phenyl-pyrrolidin-1-yl)-ethyl]-N-(3-trifluoromethyl-phenyl)-benzenesulfonamide; and N-(4-chloro-phenyl)-2-methoxy-N-[2-oxo-2-(2-phenyl-pyrrolidin-1-yl)-ethyl]-benzenesulfonamide;

Preferred compounds from this group are further those, wherein R¹ is 4-fluoro and the other definitions are as described above, for example the following compounds 2-chloro-N-(4-chloro-phenyl)-N-{2-[2-(4-fluoro-phenyl)-pyrrolidin-1-yl]-2-oxo-ethyl}-benzenesulfonamide;

N-(4-chloro-phenyl)-3-fluoro-N-{2-[2-(4-fluoro-phenyl)-pyrrolidin-1-yl]-2-oxo-ethyl}-benzenesulfonamide;

N-(4-chloro-phenyl)-2-fluoro-N-{2-[2-(4-fluoro-phenyl)-pyrrolidin-1-yl]-2-oxo-ethyl}-benzenesulfonamide;

3-chloro-N-(4-chloro-phenyl)-N-{2-[2-(4-fluoro-phenyl)-pyrrolidin-1-yl]-2-oxo-ethyl}-benzenesulfonamide;

4-chloro-N-(4-chloro-phenyl)-N-{2-[2-(4-fluoro-phenyl)-pyrrolidin-1-yl]-2-oxo-ethyl}-benzenesulfonamide;

N-(4-chloro-phenyl)-N-{2-[2-(4-fluoro-phenyl)-pyrrolidin-1-yl]-2-oxo-ethyl}-2-methyl-benzenesulfonamide;

N-(4-chloro-phenyl)-N-{2-[2-(4-fluoro-phenyl)-pyrrolidin-1-yl]-2-oxo-ethyl}-3-methoxy-benzenesulfonamide;

N-(4-chloro-phenyl)-N-{2-[2-(4-fluoro-phenyl)-pyrrolidin-yl]-2-oxo-ethyl}-methoxy-benzenesulfonamide;

N-(4-chloro-phenyl)-N-{2-[2-(4-fluoro-phenyl)-pyrrolidin-1-yl]-2-oxo-ethyl}-4-methyl-benzenesulfonamide;

N-(4-chloro-phenyl)-N-{2-[2-(4-fluoro-phenyl)-pyrrolidin-1-yl]-2-oxo-ethyl}-3-methyl-benzenesulfonamide;

N-{2-[2-(4-fluoro-phenyl)-pyrrolidin-1-yl]-2-oxo-ethyl}-4-methoxy-N-(2-methoxy-phenyl)-benzenesulfonamide;

N-(3-fluoro-phenyl)-N-{2-[2-(4-fluoro-phenyl)-pyrrolidin-1-yl]-2-oxo-ethyl}-4-methoxy-benzenesulfonamide;

N-(4-chloro-phenyl)-4-fluoro-N-{2-[2-(4-fluoro-phenyl)-pyrrolidin-1-yl]-2-oxo-ethyl}-benzenesulfonamide;

N-{2-[2-(4-fluoro-phenyl)-pyrrolidin-1-yl]-2-oxo-ethyl}-4-methoxy-N-(4-methoxy-phenyl)-benzenesulfonamide;

N-(4-fluoro-phenyl)-N-{2-[2-(4-fluoro-phenyl)-pyrrolidin-1-yl]-2-oxo-ethyl}-4-methoxy-benzenesulfonamide; and N-(4-chloro-phenyl)-N-{2-[2-(4-fluoro-phenyl)-pyrrolidin-1-yl]-2-oxo-ethyl}-2-methoxy-benzenesulfonamide.

The present compounds of formula I and their pharmaceutically acceptable salts can be prepared by methods known in the art, for example, by processes described below, which process comprises a) reacting a compound of formula

II

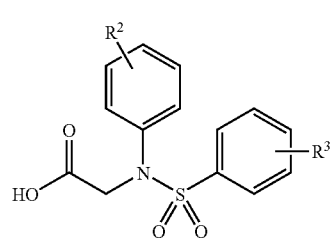

with a compound of formula

III

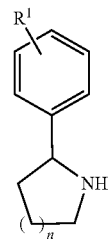

to obtain a compound of formula

I

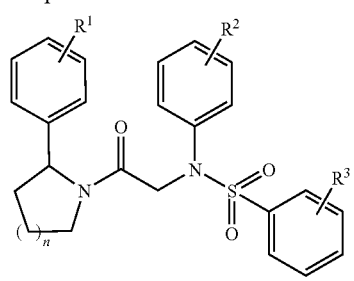

wherein the substituents are as described above, and
if desired, converting the compounds obtained into pharmaceutically acceptable acid addition salts.

General Synthetic Procedure

The preparation of compounds of formula I of the present invention can be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

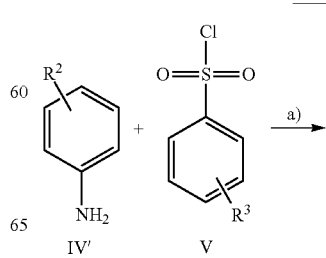

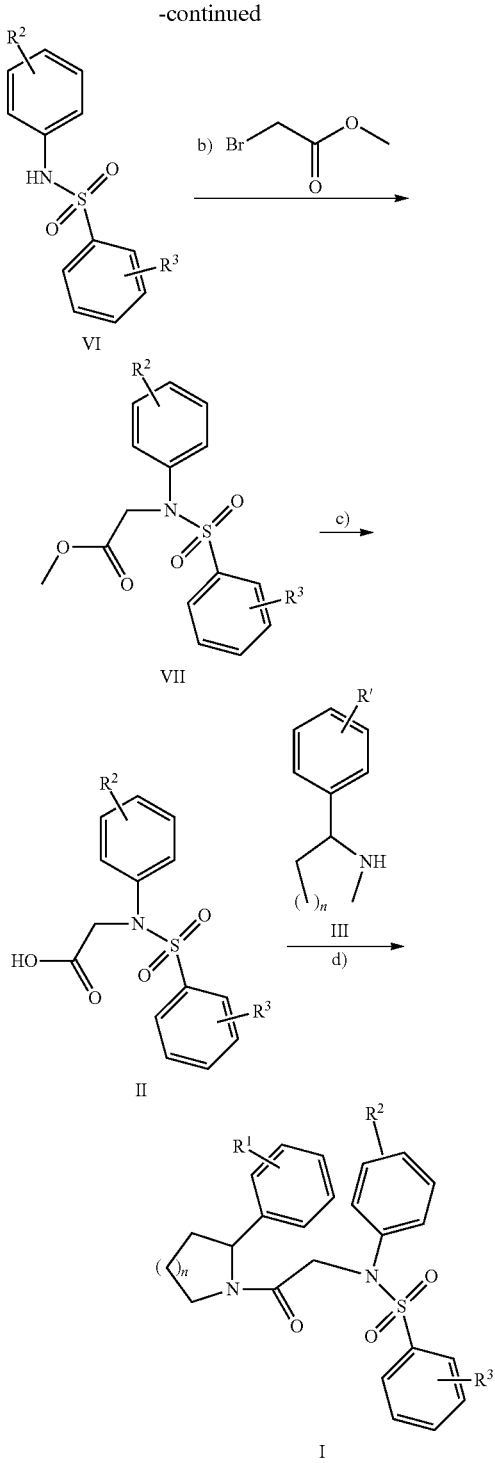

Step a)

Anilins IV and sulfonylchlorides V are commercially available or can be accessed by methods described in the literature. Reaction of aniline IV with sulfonylchlorides V can be affected by several methods as described in the literature (for reaction conditions see for example: Comprehensive Organic Transformations: A Guide to Functional Group Preparations, 2nd Edition, Richard C. Larock. John Wiley & Sons, New York, N.Y. 1999). However, it is convenient to react aniline IV with sulfonylchloride V in the presence or absence of a base and a solvent. There is no particular restriction on the nature of the solvent to be employed, provided that it has no adverse effect on the reaction or the reagents involved and that it can dissolve the reagents, at least to some extent. Examples for suitable solvents include dichloromethane (DCM) and the like. There is no particular restriction on the nature of the base used in this stage, and any base commonly used in this type of reaction can equally be employed here. Examples of such bases include pyridine and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the sulfonamide derivative VI.

Step b)

The reaction of sulfonamide derivative VI with methyl bromoacetate can be affected under various reaction condition (see for example: Journal of Medicinal Chemistry (2005), 48(24), 7882-7905.). We find it convenient to react sulfonamide derivative VI with methyl bromoacetate in the presence of a base and a solvent. There is no particular restriction on the nature of the solvent to be employed, provided that it has no adverse effect on the reaction or the reagents involved and that it can dissolve the reagents, at least to some extent. Examples for suitable solvents include tetrahydrofuran (THF), N,N-dimethylformamide (DMF) and the like. There is no particular restriction on the nature of the base used in this stage, and any base commonly used in this type of reaction can equally be employed here. Examples of such bases include sodium hydride and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the ester derivative VII.

Step c)

Transformation of ester derivatives VII into the final compounds can be done according to procedures described in literature. However, we find it convenient to employ a two step reaction sequence in which the ester functionality in VII is cleaved under aqueous basic conditions and the liberated acid functionality converted with the respective amines under coupling conditions to the respective sulfonamide derivatives II. There is no particular restriction on the nature of the aqueous base to be employed, provided that it has no adverse effect on the reaction or the reagents involved and that it can dissolve the reagents, at least to some extent. Examples for suitable aqueous bases include NaOH, LiOH and the like. Any commonly used co-solvent can be employed. Examples include THF and the like. The reaction can take place over a wide range of temperatures, and the precise reaction temperature is not critical to the invention. It is convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield the acid derivatives II.

Step d)

The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock, John Wiley & Sons, New York, N.Y. 1999). However, it is convenient to couple acid derivative II with 2-aryl-(pyrrolidine)piperidine derivatives III (either commercially available or accessible by methods described in references or by methods known in the art; as appropriate) in the presence of a coupling reagent, a base and a solvent. For example coupling reagents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction can equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction can also vary widely, depending on many factors, notably the reaction temperature and the nature of the reagents. However, a period of from 0.5 h to several days will usually suffice to yield sulfonamide derivatives I.

The compounds were investigated in accordance with the test given hereinafter.

Intracellular $Ca^{2+}$ Mobilization Assay

The Chinese Hamster Ovary (dHFr-) mutant cell line stably expressing human orexin-1 (hOX1) or human orexin-2 (hOX2) receptors were maintained in Dulbecco's Modified Eagle Medium (1X) with GlutaMax™ 1, 4500 mg/L D-Glucose and Sodium Pyruvate (Catalog No. 31966-021, Invitrogen, Carlsbad, Calif.), 5% dialyzed fetal calf serum (Catalog No. 26400-044), 100 µg/ml penicillin and 100 µg/ml streptomycin. The cells were seeded at $5\times10^4$ cells/well in the poly-D-lysine treated, 96-well, black/clear-bottomed plates (Catalog No. BD356640, BD Biosciences, Palo Alto, Calif.). 24 h later, the cells were loaded for 1 hr at 37° C. with 4 µM Flou-4 acetoxymethyl ester (Catalog No. F-14202, Molecular Probes, Eugene, Oreg.) in FLIPR buffer (1×HBSS, 20 mM HEPES, 2.5 mM Probenecid). Hanks' Balanced Salt Solution (HBSS) (10X) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with FLIPR buffer to remove excess dye and intracellular calcium mobilization, $[Ca^{2+}]$ were measured using a Fluorometric Imaging Plate Reader (FLIPR-96, Molecular Devices, Menlo Park, Calif.) as described previously (Malherbe et al., *Mol. Pharmacol.*, 64, 823-832, 2003). Orexin A (catalog No.1455, Toris Cookson Ltd, Bristol, UK) was used as agonist. Orexin A (50 mM stock solution in DMSO) was diluted in FLIPR buffer +0.1% BSA. The $EC_{50}$ and $EC_{80}$ values of orexin-A were measured daily from standard agonist concentration-response curves in CHO(dHFr-)-OX1R and —OX2R cell lines. All compounds were dissolved in 100% DMSO. Inhibition curves were determined by addition of 11 concentrations (0.0001-10 µM) of inhibitory compounds and using $EC_{80}$ value of orexin-A as agonist (a concentration which gave 80% of max agonist response, determined daily). The antagonists were applied 25 min (incubation at 37° C.) before the application of the agonist. Responses were measured as peak increase in fluorescence minus basal, normalized to the maximal stimulatory effect induced by $EC_{80}$ value of orexin-A or orexin-B. Inhibition curves were fitted according to the Hill equation: $y=100/(1+(x/IC_{50})^{nH})$, where $n_H$=slope factor using Excel-fit 4 software (Microsoft). $K_b$ values were calculated according to the following equation $K_b=IC_{50}/(1+[A]/EC_{50})$ where A is the concentration of agonist added which is very close to agonist $EC_{80}$ value, and IC50 and EC50 values were derived from the antagonist inhibition and orexin-A or B agonist curves, respectively.

The compounds show a $K_b$ value (µM)<0.01 in human on orexin receptor. Some examples are shown in the table below.

| Example | $K_b$ (µM) OX2R (human) |
|---|---|
| 1 | 0.0017 |
| 2 | 0.0049 |
| 3 | 0.0005 |
| 4 | 0.0011 |
| 5 | 0.0019 |
| 6 | 0.0042 |
| 7 | 0.0007 |
| 8 | 0.0022 |
| 9 | 0.0014 |
| 10 | 0.003 |
| 11 | 0.0005 |
| 12 | 0.0012 |
| 13 | 0.0025 |
| 15 | 0.0018 |
| 16 | 0.0009 |
| 18 | 0.0014 |
| 19 | 0.002 |
| 20 | 0.0006 |
| 21 | 0.0006 |
| 22 | 0.0017 |
| 23 | 0.0013 |
| 24 | 0.0005 |
| 26 | 0.005 |
| 27 | 0.003 |
| 31 | 0.0064 |
| 36 | 0.0077 |
| 38 | 0.0096 |
| 40 | 0.0005 |
| 41 | 0.0026 |
| 43 | 0.0032 |
| 45 | 0.0079 |
| 47 | 0.0077 |
| 50 | 0.0018 |
| 52 | 0.0003 |

The present invention also provides pharmaceutical compositions containing compounds of the invention, for example compounds of formula (I) and their pharmaceutically acceptable acid addition salts, and a pharmaceutically acceptable carrier. Such pharmaceutical compositions can be in the form of tablets, coated tablets, dragees, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, drages and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include sleep disorders including sleep apnea, narcolepsy, insomnia, parasomnia, jet lag syndrome, circadian rhythms disorder, restless leg syndrome, psychiatric, neurological and neurodegenerative disorders including anxiety, depression, manic depression, obsessive compulsive disorders, affective neurosis, depressive neurosis, anxiety neurosis, mood disorder, delirium, panic-attack disorder, posttraumatic stress disorders, sexual dysfunction, schizophrenia, psychosis, cognitive disorders, Alzheimer's and Parkinson's diseases, dementia, mental retardation, dyskinesias such as Huntington's disease and Tourette syndrome, addictions, craving associated with drug abuse, seizure disorders, epilepsy, metabolic diseases such as obesity, diabetes, eating disorders including anorexia and bulimia, asthma, migraine, pain, neuropathic pain, sleep disorders associated with psychiatric, neurological and neurodegenerative disorders, neuropathic pain, enhanced or exaggerated sensitivity to pain such as hyperalgesia, causalgia, and aflodynia, acute pain, burn pain, back pain, complex regional pain syndrome I and II, arthritic pain, post-stroke pain, post-operative pain, neuralgia, pain associated with HIV infection, post-chemotherapy pain, irritable bowel syndrome and other diseases related to general orexin system dysfunction.

The dosage at which compounds of the invention can be administered can vary within wide limits and will, of course, have to be adjusted to the individual requirements in each particular case. In the case of oral administration the dosage f)r adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | | |
|---|---|---|---|---|---|
| | | mg/tablet | | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | | |
|---|---|---|---|---|---|
| | | mg/capsule | | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

Experimental Part:

Example 1

N-(4-Chloro-phenyl)-3-methoxy-N-[2-oxo-2-(2-phenyl-pyrrolidin-1-yl)-ethyl]-benzenesulfonamide

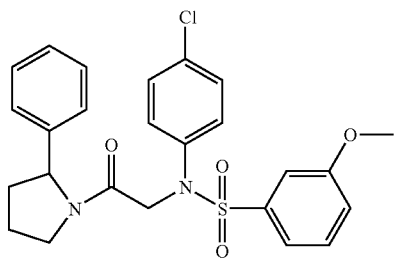

13 a) step 1:

N-(4-Chlorophenyl)-3-methoxy-benzenesulfonamide

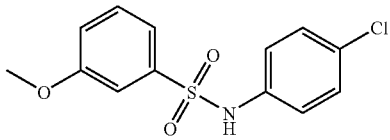

To a solution of 4-chloroaniline (400 mg, 3.13 mmol) in anhydrous dichloromethane (40 mL) were added 3-methoxy-benzenesulfonyl chloride (648 mg, 3.13 mmol) followed by pyridine (297.2 mg, 3.76 mmol). The mixture was allowed to stir for 12 h at 25° C. 10% citric acid solution (20 mL) and water (20 mL) was added. The organic phase was dried ($Na_2SO_4$), and evaporated under reduced pressure yielding the title compound as solid which was used as such in the next step. Yield: 900 mg (96%). MS (m/e): 296 ($M^+$–H); $^1$H-NMR ($CDCl_3$, 400 MHz): δ 3.76 (s, 3H), 6.48 (brs, 1H), 7.0 (d, J=8.72 Hz, 2H), 7.06 (d, J=7.76 Hz, 1H), 7.21 (m, 3H), 7.32 (m, 2H).

b) Step 2:

[(4-Chlorophenyl)-(3-methoxy-benzenesulphonyl)-amino]-acetic acid methyl ester

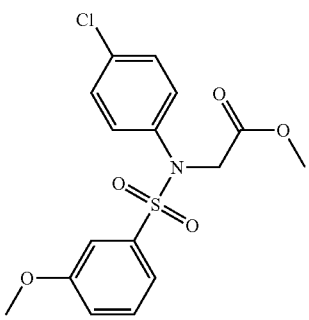

To a solution of N-(4-chlorophenyl)-3-methoxy-benzenesulfonamide (900 mg, 3.02 mmol) in anhydrous THF (40 mL) was added sodium hydride (146 mg, 3.62 mmol) at 0-5° C. under nitrogen. The mixture was stirred at 25° C. for 30 minutes. Methyl bromoacetate (463 mg, 3.02 mmol) was then added, stirred for 1 h at 25° C. A further amount of methyl bromoacetate (232 mg, 1.51 mmol) was added, and stirring continued for another 12 h. The reaction mixture was quenched with saturated aqueous ammonium chloride solution, and extracted with ethyl acetate (3×20 ml). The combined organic layer was washed with water, dried ($Na_2SO_4$), evaporated under reduced pressure to yield the title compound as oily compound, which was used as such in the next step. Yield: 1.03 g (92%).

c) Step 3:

[(4-Chlorophenyl)-(3-methoxy-benzenesulfonyl)-amino]-acetic acid (intermediate 1)

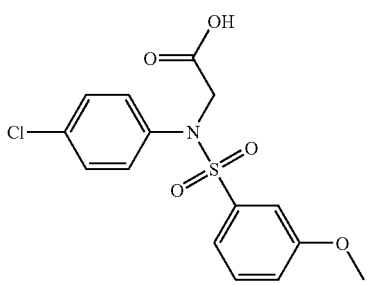

To a solution of [(4-chlorophenyl)-(3-methoxy-benzenesulfonyl)-amino]-acetic acid methyl ester (1.03 g, 2.7 mmol) in THF (20 mL) was added an aqueous solution (10 mL) of lithium hydroxide monohydrate (168 mg, 4.0 mmol) slowly under ice-cooled condition. The reaction mixture was stirred for 2 h at 25° C. THF was evaporated in vacuo and water was added. The mixture was washed with diethyl ether. The aqueous layer was acidified with 1(N) hydrochloride acid to pH 6, and extracted with ethyl acetate (3×20 mL). The combined organic layers were washed with water, dried ($Na_2SO_4$), and evaporated under reduced pressure to yield the title compound as pure solid compound, which used as such in the final coupling reaction. Yield: 810 mg (84%).

d) Step 4:

N-(4-Chloro-phenyl)-3-methoxy-N-[2-oxo-2-(2-phenyl-pyrrolidin-1-yl)-ethyl]-benzene sulfonamide

To a solution of [(4-chlorophenyl)-(3-methoxy-benzenesulfonyl)-amino]-acetic acid (250 mg, 0.7 mmol) in dry dichloromethane (20 mL) were sequentially added EDCI (202 mg, 1.05 mmol), HOBT (142.4 mg, 1.05 mmol), and DIPEA (0.23 mL, 1.40 mmol). The reaction mixture was allowed to stir for 30 minutes under nitrogen at 25° C. 2-Phenyl-pyrrolidine (104 mg, 0.7 mmol) was added and the mixture was stirred at 25° C. for 12 h. The reaction mixture was diluted with dichloromethane (20 mL), washed with saturated aqueous ammonium chloride solution, saturated aqueous sodium bicarbonate solution and water. The organic layer was dried ($Na_2SO_4$) and evaporated under reduced pressure. The residue was purified by column chromatography over silica gel (30-40% ethyl acetate/hexane) to yield the title compound.

Yield: 140 mg (41%). HPLC purity 98.17%; MS (m/e): 485.4 ($M^+$+H); $^1$H-NMR (DMSO-$d_6$, 400 MHz): δ1.76 (m, 1H), 1.85 (m, 3H), 2.32 (m, 1H), 3.45 (m, 1H), 3.78 (s, 3H), 4.77 (m, 3H), 6.93 (m, 3H), 7.19 (m, 6H), 7.43 (m, 4H).

In analogy to the procedure described for the synthesis of [(4-chlorophenyl)-(3-methoxy-benzenesulfonyl)-amino]-acetic acid (example 1, step 3) further intermediate acids have been synthesized by reaction of the respective aniline with the respective sulfonyl chloride and methyl bromacetate and subsequent saponification with LiOH. The intermediate acids and the respective starting materials are shown in table 1 and comprise intermediate 2-intermediate 25.

TABLE 1

| No. | Intermediate acid | MW | name | Starting materials |
|---|---|---|---|---|
| 2 | 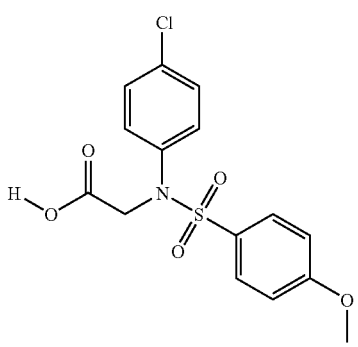 | 355.8 | [(4-Chloro-phenyl)-(4-methoxy-benzenesulfonyl)-amino]-acetic acid | 4-Chloro-phenylamine, 4-Methoxy-benzenesulfonyl chloride and Bromo-acetic acid methyl ester (all commercially available) |
| 3 | 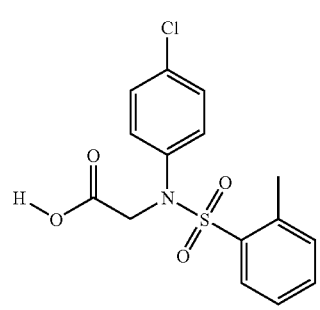 | 339.8 | [(4-Chloro-phenyl)-(toluene-2-sulfonyl)-amino]-acetic acid | 4-Chloro-phenylamine, 2-Methyl-benzenesulfonyl chloride and Bromo-acetic acid methyl ester (all commercially available) |
| 4 | 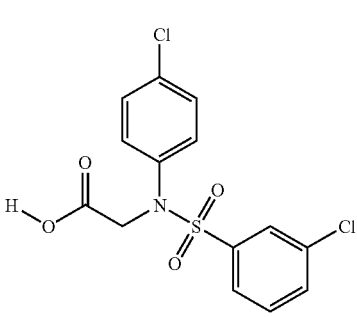 | 360.2 | [(3-Chloro-benzenesulfonyl)-(4-chloro-phenyl)-amino]-acetic acid | 4-Chloro-phenylamine, 3-Chloro-benzenesulfonyl chloride and Bromo-acetic acid methyl ester (all commercially available) |
| 5 | 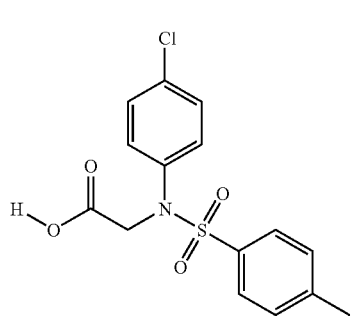 | 339.8 | [(4-Chloro-phenyl)-(toluene-4-sulfonyl)-amino]-acetic acid | 4-Chloro-phenylamine, 4-Methyl-benzenesulfonyl chloride and Bromo-acetic acid methyl ester (all commercially available) |
| 6 | 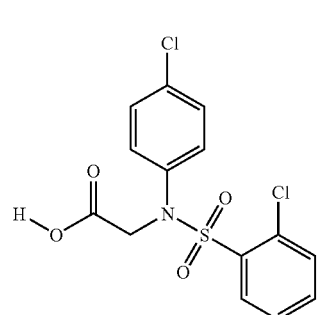 | 360.2 | [(2-Chloro-benzenesulfonyl)-(4-chloro-phenyl)-amino]-acetic acid | 4-Chloro-phenylamine, 2-Chloro-benzenesulfonyl chloride and Bromo-acetic acid methyl ester (all commercially available) |

TABLE 1-continued

| No. | Intermediate acid | MW | name | Starting materials |
|---|---|---|---|---|
| 7 | | 360.2 | [(4-Chloro-benzenesulfonyl)-(4-chloro-phenyl)-amino]-acetic acid | 4-Chloro-phenylamine, 4-Chloro-benzenesulfonyl chloride and Bromo-acetic acid methyl ester (all commercially available) |
| 8 | | 343.7 | [(4-Chloro-phenyl)-(4-fluoro-benzenesulfonyl)-amino]-acetic acid | 4-Chloro-phenylamine, 4-Fluoro-benzenesulfonyl chloride and Bromo-acetic acid methyl ester (all commercially available) |
| 9 | | 343.7 | [(4-Chloro-phenyl)-(3-fluoro-benzenesulfonyl)-amino]-acetic acid | 4-Chloro-phenylamine, 3-Fluoro-benzenesulfonyl chloride and Bromo-acetic acid methyl ester (all commercially available) |
| 10 | | 339.8 | [(4-Chloro-phenyl)-(toluene-3-sulfonyl)-amino]-acetic acid | 4-Chloro-phenylamine, 3-Methyl-benzenesulfonyl chloride and Bromo-acetic acid methyl ester (all commercially available) |
| 11 | | 343.7 | [(4-Chloro-phenyl)-(2-fluoro-benzenesulfonyl)-amino]-acetic acid | 4-Chloro-phenylamine, 2-Fluoro-benzenesulfonyl chloride and Bromo-acetic acid methyl ester (all commercially available) |

TABLE 1-continued

| No. | Intermediate acid | MW | name | Starting materials |
|---|---|---|---|---|
| 12 | 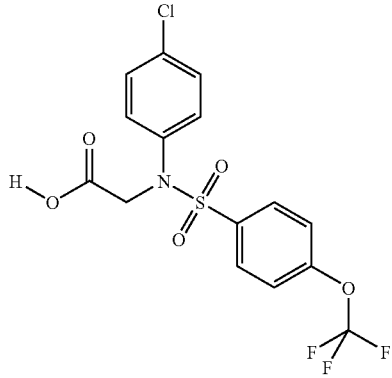 | 409.8 | [(4-Chloro-phenyl)-(4-trifluoromethoxy-benzenesulfonyl)-amino]-acetic acid | 4-Chloro-phenylamine, 4-Trifluoromethoxy-benzenesulfonyl chloride and Bromo-acetic acid methyl ester (all commercially available) |
| 13 | 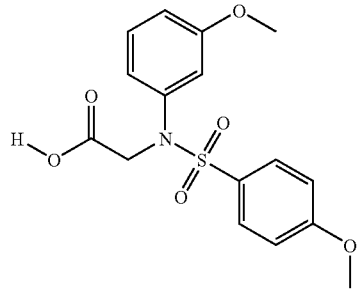 | 351.4 | [(4-Methoxy-benzenesulfonyl)-(3-methoxy-phenyl)-amino]-acetic acid | 3-Methoxy-phenylamine, 4-Methoxy-benzenesulfonyl chloride and Bromo-acetic acid methyl ester (all commercially available) |
| 14 | 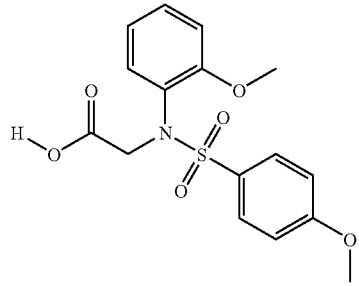 | 351.4 | [(4-Methoxy-benzenesulfonyl)-(2-methoxy-phenyl)-amino]-acetic acid | 2-Methoxy-phenylamine, 4-Methoxy-benzenesulfonyl chloride and Bromo-acetic acid methyl ester (all commercially available) |
| 15 | 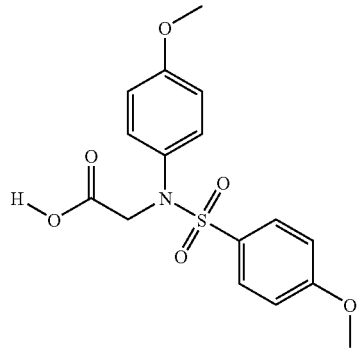 | 351.4 | [(4-Methoxy-benzenesulfonyl)-(4-methoxy-phenyl)-amino]-acetic acid | 4-Methoxy-phenylamine, 4-Methoxy-benzenesulfonyl chloride and Bromo-acetic acid methyl ester (all commercially available) |

TABLE 1-continued

| No. | Intermediate acid | MW | name | Starting materials |
|---|---|---|---|---|
| 16 | | 391.8 | [(4-Chloro-phenyl)-(4-difluoromethoxy-benzenesulfonyl)-amino]-acetic acid | 4-Chloro-phenylamine, 4-Difluoromethoxy-benzenesulfonyl chloride and Bromo-acetic acid methyl ester (all commercially available) |
| 17 | | 339.3 | [(3-Fluoro-phenyl)-(4-methoxy-benzenesulfonyl)-amino]-acetic acid | 4-Fluoro-phenylamine, 4-Methoxy-benzenesulfonyl chloride and Bromo-acetic acid methyl ester (all commercially available) |
| 18 | | 389.3 | [(4-Methoxy-benzenesulfonyl)-(4-trifluoromethyl-phenyl)-amino]-acetic acid | 4-Trifluoromethyl-phenylamine, 4-Methoxy-benzenesulfonyl chloride and Bromo-acetic acid methyl ester (all commercially available) |
| 19 | | 389.3 | [(4-Methoxy-benzenesulfonyl)-(3-trifluoromethyl-phenyl)-amino]-acetic acid | 3-Trifluoromethyl-phenylamine, 4-Methoxy-benzenesulfonyl chloride and Bromo-acetic acid methyl ester (all commercially available) |

TABLE 1-continued

| No. | Intermediate acid | MW | name | Starting materials |
|---|---|---|---|---|
| 20 | (structure) | 389.3 | [(4-Methoxy-benzenesulfonyl)-(2-trifluoromethyl-phenyl)-amino]-acetic acid | 2-Trifluoromethyl-phenylamine, 4-Methoxy-benzenesulfonyl chloride and Bromo-acetic acid methyl ester (all commercially available) |
| 21 | (structure) | 355.8 | [(3-Chloro-phenyl)-(4-methoxy-benzenesulfonyl)-amino]-acetic acid | 3-Chloro-phenylamine, 4-Methoxy-benzenesulfonyl chloride and Bromo-acetic acid methyl ester (all commercially available) |
| 22 | (structure) | 339.3 | [(2-Fluoro-phenyl)-(4-methoxy-benzenesulfonyl)-amino]-acetic acid | 2-Fluoro-phenylamine, 4-Methoxy-benzenesulfonyl chloride and Bromo-acetic acid methyl ester (all commercially available) |
| 23 | (structure) | 339.3 | [(4-Fluoro-phenyl)-(4-methoxy-benzenesulfonyl)-amino]-acetic acid | 4-Fluoro-phenylamine, 4-Methoxy-benzenesulfonyl chloride and Bromo-acetic acid methyl ester (all commercially available) |
| 24 | (structure) | 355.8 | [(2-Chloro-phenyl)-(4-methoxy-benzenesulfonyl)-amino]-acetic acid | 2-Chloro-phenylamine, 4-Methoxy-benzenesulfonyl chloride and Bromo-acetic acid methyl ester (all commercially available) |

TABLE 1-continued

| No. | Intermediate acid | MW | name | Starting materials |
|---|---|---|---|---|
| 25 | | 355.8 | [(4-Chloro-phenyl)-(2-methoxy-benzenesulfonyl)-amino]-acetic acid | 4-Chloro-phenylamine, 2-methoxy-benzenesulfonyl chloride and Bromo-acetic acid methyl ester (all commercially available) |

In analogy to the procedure described for the synthesis of N-(4-Chloro-phenyl)-4-methoxy-N-[2-oxo-2-(2-phenyl-pyrrolidin-1-yl)-ethyl]-benzenesulfonamide (example 1, step 4) further sulfonamide derivatives have been synthesized from the respective starting materials mentioned in table 2. Table 2 comprises example 2 to 53.

TABLE 2

| No | structure | MW | Systematic Name | starting material | MW found |
|---|---|---|---|---|---|
| 2 | 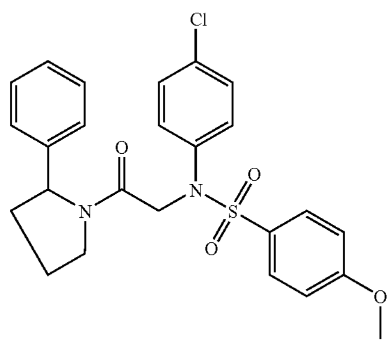 | 485.0 | N-(4-Chloro-phenyl)-4-methoxy-N-[2-oxo-2-(2-phenyl-pyrrolidin-1-yl)-ethyl]-benzenesulfonamide | [(4-Chloro-phenyl)-(4-methoxy-benzenesulfonyl)-amino]-acetic acid, and 2-phenylpyrrolidine (commercially available) | 485.4 |
| 3 | 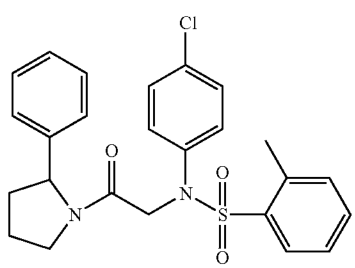 | 469.0 | N-(4-Chloro-phenyl)-2-methyl-N-[2-oxo-2-(2-phenyl-pyrrolidin-1-yl)-ethyl]-benzenesulfonamide | [(4-Chloro-phenyl)-(toluene-2-sulfonyl)-amino]-acetic acid, and 2-phenylpyrrolidine (commercially available) | 469.5 |
| 4 | 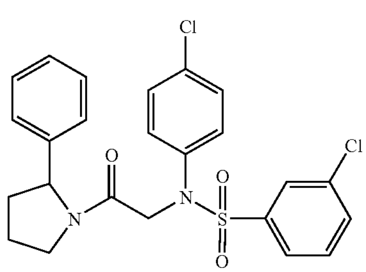 | 489.4 | 3-Chloro-N-(4-chloro-phenyl)-N-[2-oxo-2-(2-phenyl-pyrrolidin-1-yl)-ethyl]-benzenesulfonamide | [(3-Chloro-benzenesulfonyl)-(4-chloro-phenyl)-amino]-acetic acid, and 2-phenylpyrrolidine (commercially available) | 489.4 |

TABLE 2-continued

| No | structure | MW | Systematic Name | starting material | MW found |
|---|---|---|---|---|---|
| 5 | 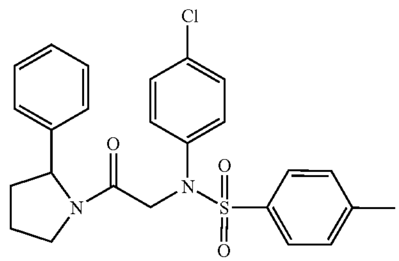 | 469.0 | N-(4-Chloro-phenyl)-4-methyl-N-[2-oxo-2-(2-phenyl-pyrrolidin-1-yl)-ethyl]-benzenesulfonamide | [(4-Chloro-phenyl)-(toluene-4-sulfonyl)-amino]-acetic acid, and and 2-phenylpyrrolidine (commercially available) | 469.5 |
| 6 | 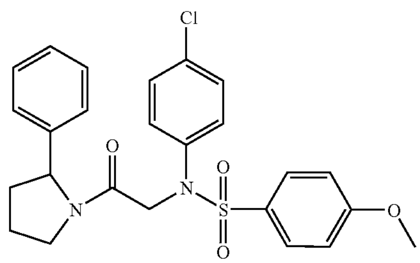 | 485.0 | N-(4-Chloro-phenyl)-4-methoxy-N-[2-oxo-2-(2-phenyl-pyrrolidin-1-yl)-ethyl]-benzenesulfonamide | [(4-Chloro-phenyl)-(4-methoxy-benzenesulfonyl)-amino]-acetic acid, and 2-phenylpyrrolidine (commercially available) | 485.4 |
| 7 | 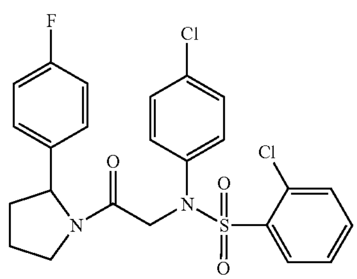 | 507.4 | 2-Chloro-N-(4-chloro-phenyl)-N-{2-[2-(4-fluoro-phenyl)-pyrrolidin-1-yl]-2-oxo-ethyl}-benzenesulfonamide | [(2-Chloro-benzenesulfonyl)-(4-chloro-phenyl)-amino]-acetic acid, and 2-(4-Fluoro-phenyl)-pyrrolidine (commercially available) | 507.4 |
| 8 | 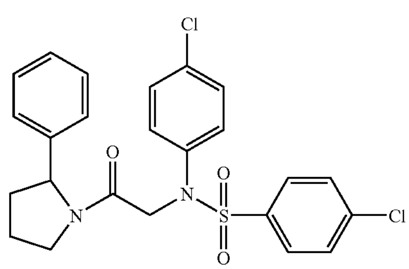 | 489.4 | 4-Chloro-N-(4-chloro-phenyl)-N-[2-oxo-2-(2-phenyl-pyrrolidin-1-yl)-ethyl]-benzenesulfonamide | [(4-Chloro-benzenesulfonyl)-(4-chloro-phenyl)-amino]-acetic acid, and 2-phenylpyrrolidine (commercially available) | 489.4 |
| 9 | 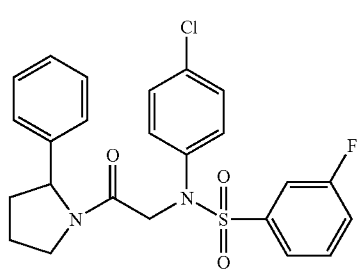 | 473.0 | N-(4-Chloro-phenyl)-4-fluoro-N-[2-oxo-2-(2-phenyl-pyrrolidin-1-yl)-ethyl]-benzenesulfonamide | [(4-Chloro-phenyl)-(4-fluoro-benzenesulfonyl)-amino]-acetic acid, and 2-phenylpyrrolidine (commercially available) | 473.3 |

TABLE 2-continued

| No | structure | MW | Systematic Name | starting material | MW found |
|---|---|---|---|---|---|
| 10 | 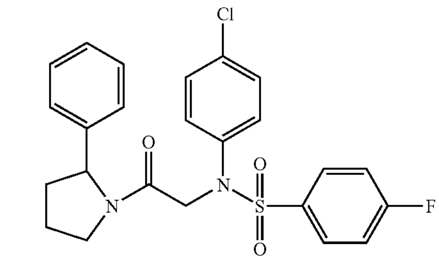 | 473.0 | N-(4-Chloro-phenyl)-3-fluoro-N-[2-oxo-2-(2-phenyl-pyrrolidin-1-yl)-ethyl]-benzenesulfonamide | [(4-Chloro-phenyl)-(3-fluoro-benzene sulfonyl)-amino]-acetic acid, and 2-phenylpyrrolidine (commercially available) | 473.5 |
| 11 | 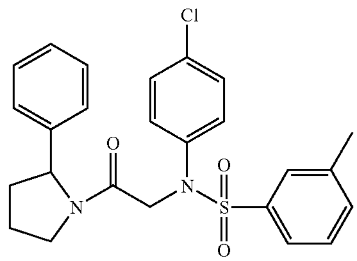 | 469.0 | N-(4-Chloro-phenyl)-3-methyl-N-[2-oxo-2-(2-phenyl-pyrrolidin-1-yl)-ethyl]-benzenesulfonamide | [(4-Chloro-phenyl)-(toluene-3-sulfonyl)-amino]-acetic acid, and 2-phenylpyrrolidine (commercially available) | 469.4 |
| 12 | 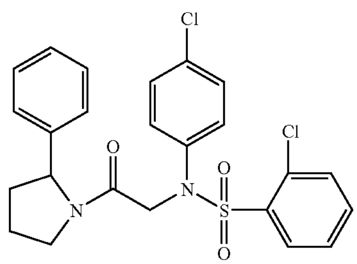 | 489.4 | 2-Chloro-N-(4-chloro-phenyl)-N-[2-oxo-2-(2-phenyl-pyrrolidin-1-yl)-ethyl]-benzenesulfonamide | [(2-Chloro-benzenesulfonyl)-(4-chloro-phenyl)-amino]-acetic acid, and 2-phenylpyrrolidine (commercially available) | 489.3 |
| 13 | 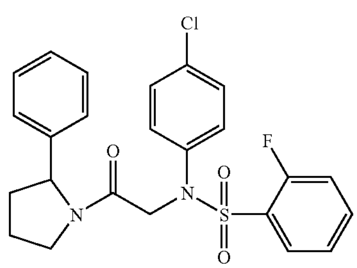 | 473.0 | N-(4-Chloro-phenyl)-2-fluoro-N-[2-oxo-2-(2-phenyl-pyrrolidin-1-yl)-ethyl]-benzenesulfonamide | [(4-Chloro-phenyl)-(2-fluoro-benzene sulfonyl)-amino]-acetic acid, and 2-phenylpyrrolidine (commercially available) | 473.6 |
| 14 | 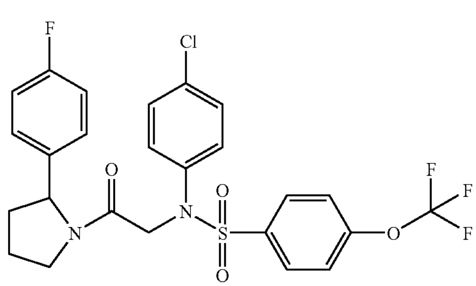 | 557.0 | N-(4-Chloro-phenyl)-N-{2-[2-(4-fluoro-phenyl)-pyrrolidin-1-yl]-2-oxo-ethyl}-4-trifluoromethoxy-benzenesulfonamide | [(4-Chloro-phenyl)-(4-trifluoromethoxy-benzenesulfonyl)-amino]-acetic acid, and 2-(4-Fluoro-phenyl)-pyrrolidine (commercially available) | 557.5 |

TABLE 2-continued

| No | structure | MW | Systematic Name | starting material | MW found |
|---|---|---|---|---|---|
| 15 | 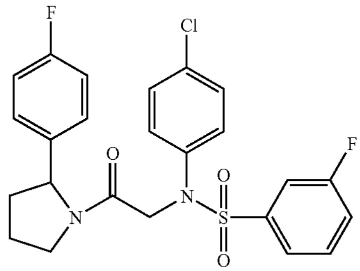 | 491.0 | N-(4-Chloro-phenyl)-3-fluoro-N-{2-[2-(4-fluoro-phenyl)-pyrrolidin-1-yl]-2-oxo-ethyl}-benzenesulfonamide | [(4-Chloro-phenyl)-(3-fluoro-benzenesulfonyl)-amino]-acetic acid, and 2-(4-Fluoro-phenyl)-pyrrolidine (commercially available) | 491.4 |
| 16 | 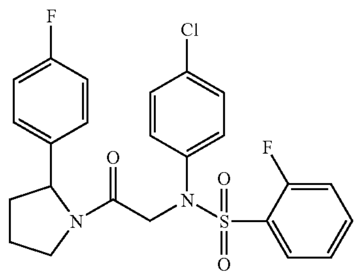 | 491.0 | N-(4-Chloro-phenyl)-2-fluoro-N-{2-[2-(4-fluoro-phenyl)-pyrrolidin-1-yl]-2-oxo-ethyl}-benzenesulfonamide | [(4-Chloro-phenyl)-(2-fluoro-benzenesulfonyl)-amino]-acetic acid, and 2-(4-Fluoro-phenyl)-pyrrolidine (commercially available) | 491.3 |
| 17 | 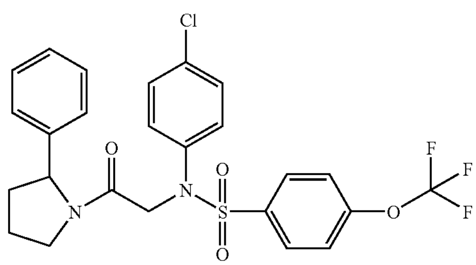 | 539.0 | N-(4-Chloro-phenyl)-N-[2-oxo-2-(2-phenyl-pyrrolidin-1-yl)-ethyl]-4-trifluoromethoxy-benzenesulfonamide | [(4-Chloro-phenyl)-(4-trifluoromethoxy-benzenesulfonyl)-amino]-acetic acid, and 2-Phenyl-pyrrolidine (commercially available) | 539.3 |
| 18 | 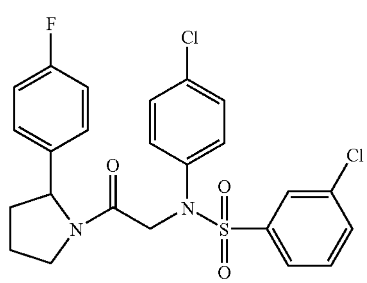 | 507.4 | 3-Chloro-N-(4-chloro-phenyl)-N-{2-[2-(4-fluoro-phenyl)-pyrrolidin-1-yl]-2-oxo-ethyl}-benzenesulfonamide | [(3-Chloro-benzenesulfonyl)-(4-chloro-phenyl)-amino]-acetic acid, and 2-(4-Fluoro-phenyl)-pyrrolidine (commercially available) | 507.3 |
| 19 | 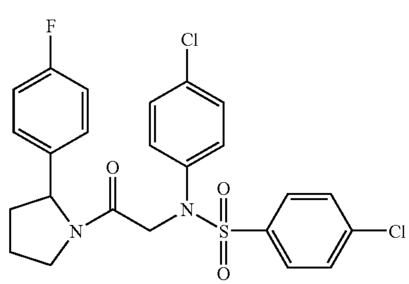 | 507.4 | 4-Chloro-N-(4-chloro-phenyl)-N-{2-[2-(4-fluoro-phenyl)-pyrrolidin-1-yl]-2-oxo-ethyl}-benzenesulfonamide | [(4-Chloro-benzenesulfonyl)-(4-chloro-phenyl)-amino]-acetic acid, and 2-(4-Fluoro-phenyl)-pyrrolidine (commercially available) | 507.4 |

TABLE 2-continued

| No | structure | MW | Systematic Name | starting material | MW found |
|----|-----------|------|-----------------|-------------------|----------|
| 20 | 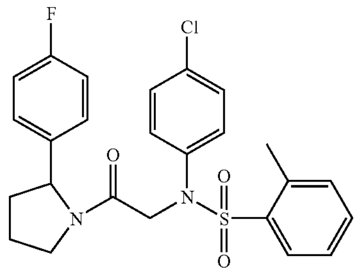 | 487.0 | N-(4-Chloro-phenyl)-N-{2-[2-(4-fluoro-phenyl)-pyrrolidin-1-yl]-2-oxo-ethyl}-2-methyl-benzenesulfonamide | [(4-Chloro-phenyl)-(toluene-2-sulfonyl)-amino]-acetic acid, and 2-(4-Fluoro-phenyl)-pyrrolidine (commercially available) | 487.5 |
| 21 | 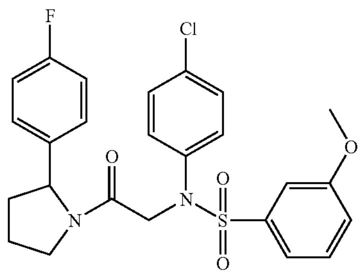 | 503.0 | N-(4-Chloro-phenyl)-N-{2-[2-(4-fluoro-phenyl)-pyrrolidin-1-yl]-2-oxo-ethyl}-3-methoxy-benzenesulfonamide | [(4-Chloro-phenyl)-(3-methoxy-benzenesulfonyl)-amino]-acetic acid, and 2-(4-Fluoro-phenyl)-pyrrolidine (commercially available) | 503.4 |
| 22 | 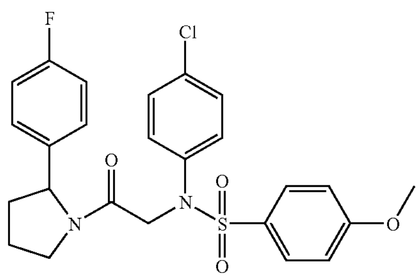 | 503.0 | N-(4-Chloro-phenyl)-N-{2-[2-(4-fluoro-phenyl)-pyrrolidin-1-yl]-2-oxo-ethyl}-4-methoxy-benzenesulfonamide | [(4-Chloro-phenyl)-(4-methoxy-benzenesulfonyl)-amino]-acetic acid, and 2-(4-Fluoro-phenyl)-pyrrolidine (commercially available) | 503.6 |
| 23 | 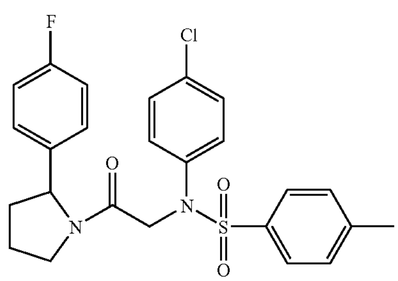 | 487.0 | N-(4-Chloro-phenyl)-N-{2-[2-(4-fluoro-phenyl)-pyrrolidin-1-yl]-2-oxo-ethyl}-4-methyl-benzenesulfonamide | [(4-Chloro-phenyl)-(toluene-4-sulfonyl)-amino]-acetic acid, and 2-(4-Fluoro-phenyl)-pyrrolidine (commercially available) | 487.5 |
| 24 | 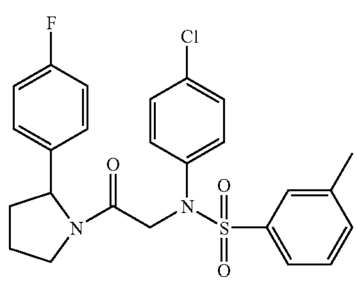 | 487.0 | N-(4-Chloro-phenyl)-N-{2-[2-(4-fluoro-phenyl)-pyrrolidin-1-yl]-2-oxo-ethyl}-3-methyl-benzenesulfonamide | [(4-Chloro-phenyl)-(toluene-3-sulfonyl)-amino]-acetic acid, and 2-(4-Fluoro-phenyl)-pyrrolidine (commercially available) | 487.5 |

TABLE 2-continued

| No | structure | MW | Systematic Name | starting material | MW found |
|---|---|---|---|---|---|
| 25 | 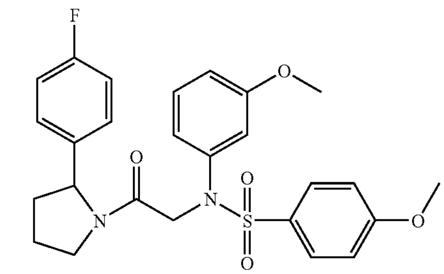 | 498.6 | N-{2-[2-(4-Fluoro-phenyl)-pyrrolidin-1-yl]-2-oxo-ethyl}-4-methoxy-N-(3-methoxy-phenyl)-benzenesulfonamide | [(4-Methoxy-benzenesulfonyl)-(3-methoxy-phenyl)amino]-acetic acid, and 2-(4-Fluoro-phenyl)-pyrrolidine (commercially available) | 499.4 |
| 26 | 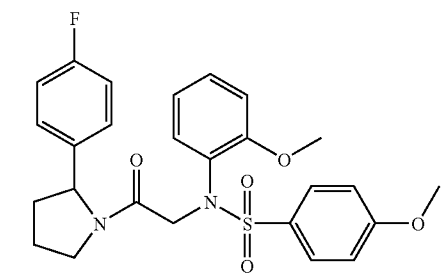 | 498.6 | N-{2-[2-(4-Fluoro-phenyl)-pyrrolidin-1-yl]-2-oxo-ethyl}-4-methoxy-N-(2-methoxy-phenyl)-benzenesulfonamide | [(4-Methoxy-benzenesulfonyl)-(2-methoxy-phenyl)-amino]-acetic acid, and 2-(4-Fluoro-phenyl)-pyrrolidine (commercially available) | 499.5 |
| 27 | 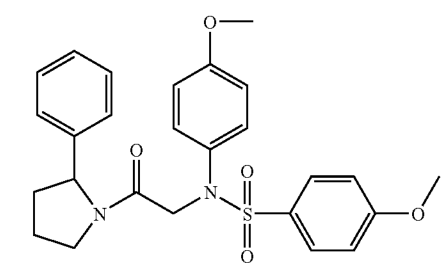 | 480.6 | 4-Methoxy-N-(4-methoxy-phenyl)-N-[2-oxo-2-(2-phenyl-pyrrolidin-1-yl)-ethyl]-benzenesulfonamide | [(4-Methoxy-benzenesulfonyl)-(4-methoxy-phenyl)-amino]-acetic acid, and 2-Phenyl-pyrrolidine (commercially available) | 481.5 |
| 28 | 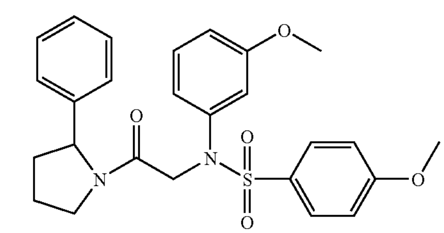 | 480.6 | 4-Methoxy-N-(3-methoxy-phenyl)-N-[2-oxo-2-(2-phenyl-pyrrolidin-1-yl)-ethyl]-benzenesulfonamide | [(4-Methoxy-benzenesulfonyl)-(3-methoxy-phenyl)-amino]-acetic acid, and 2-Phenyl-pyrrolidine (commercially available) | 481.5 |
| 29 | 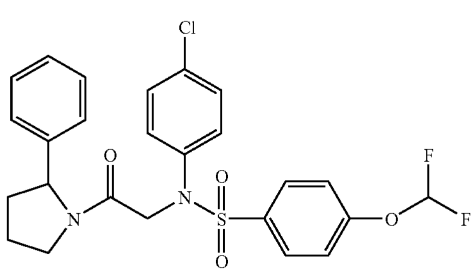 | 521.0 | N-(4-Chloro-phenyl)-4-difluoromethoxy-N-[2-oxo-2-(2-phenyl-pyrrolidin-1-yl)-ethyl]-benzenesulfonamide | [(4-Chloro-phenyl)-(4-difluoromethoxy-benzenesulfonyl)-amino]-acetic acid, and 2-Phenyl-pyrrolidine (commercially available) | 521.4 |

TABLE 2-continued

| No | structure | MW | Systematic Name | starting material | MW found |
|---|---|---|---|---|---|
| 30 | 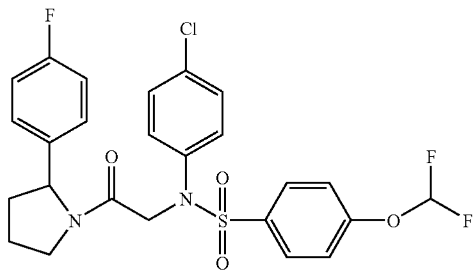 | 539.0 | N-(4-Chloro-phenyl)-4-difluoromethoxy-N-{2-[2-(4-fluoro-phenyl)-pyrrolidin-1-yl]-2-oxo-ethyl}-benzenesulfonamide | [(4-Chloro-phenyl)-(4-difluoromethoxy-benzenesulfonyl)-amino]-acetic acid, and 2-(4-Fluoro-phenyl)-pyrrolidine (commercially available) | 539.5 |
| 31 | 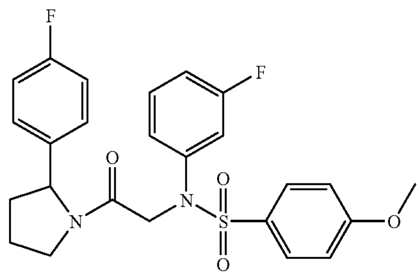 | 486.5 | N-(3-Fluoro-phenyl)-N-{2-[2-(4-fluoro-phenyl)-pyrrolidin-1-yl]-2-oxo-ethyl}-4-methoxy-benzenesulfonamide | [(3-Fluoro-phenyl)-(4-methoxy-benzenesulfonyl)-amino]-acetic acid, and 2-(4-Fluoro-phenyl)-pyrrolidine (commercially available) | 487.5 |
| 32 | 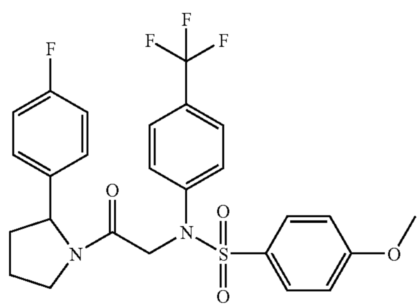 | 536.5 | N-{2-[2-(4-Fluoro-phenyl)-pyrrolidin-1-yl]-2-oxo-ethyl}-4-methoxy-N-(4-trifluoromethyl-phenyl)-benzenesulfonamide | [(4-Methoxy-benzenesulfonyl)-(4-trifluoromethyl-phenyl)-amino]-acetic acid, and 2-(4-Fluoro-phenyl)-pyrrolidine (commercially available) | 537.4 |
| 33 | 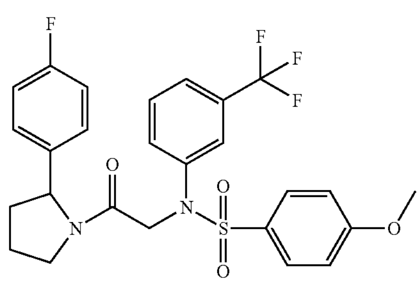 | 536.5 | N-{2-[2-(4-Fluoro-phenyl)-pyrrolidin-1-yl]-2-oxo-ethyl}-4-methoxy-N-(3-trifluoromethyl-phenyl)-benzenesulfonamide | [(4-Methoxy-benzenesulfonyl)-(3-trifluoromethyl-phenyl)-amino]-acetic acid, and 2-(4-Fluoro-phenyl)-pyrrolidine (commercially available) | 537.5 |
| 34 | 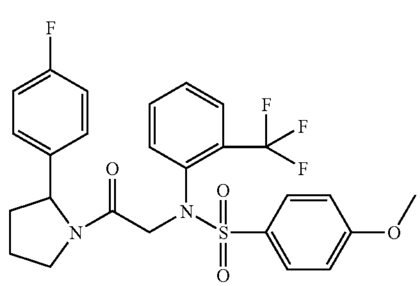 | 536.5 | N-{2-[2-(4-Fluoro-phenyl)-pyrrolidin-1-yl]-2-oxo-ethyl}-4-methoxy-N-(2-trifluoromethyl-phenyl)-benzenesulfonamide | [(4-Methoxy-benzenesulfonyl)-(2-trifluoromethyl-phenyl)-amino]-acetic acid, and 2-(4-Fluoro-phenyl)-pyrrolidine | 537.6 |

TABLE 2-continued

| No | structure | MW | Systematic Name | starting material | MW found |
|----|-----------|-----|-----------------|-------------------|----------|
| 35 | 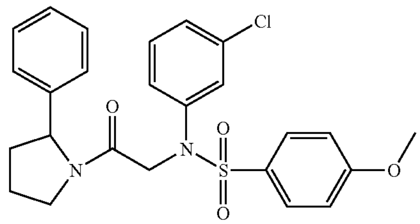 | 485.0 | N-(3-Chloro-phenyl)-4-methoxy-N-[2-oxo-2-(2-phenyl-pyrrolidin-1-yl)-ethyl]-benzenesulfonamide | [(3-Chloro-phenyl)-(4-methoxy-benzenesulfonyl)-amino]-acetic acid, and 2-Phenyl-pyrrolidine (commercially available) | 485.3 |
| 36 | 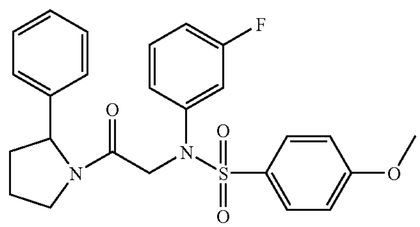 | 468.5 | N-(3-Fluoro-phenyl)-4-methoxy-N-[2-oxo-2-(2-phenyl-pyrrolidin-1-yl)-ethyl]-benzenesulfonamide | [(3-Fluoro-phenyl)-(4-methoxy-benzenesulfonyl)-amino]-acetic acid, and 2-Phenyl-pyrrolidine (commercially available) | 469.4 |
| 37 | 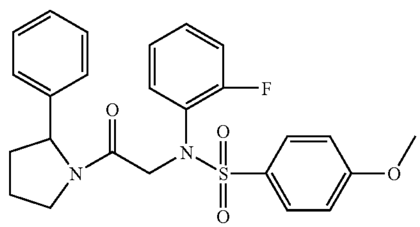 | 468.5 | N-(2-Fluoro-phenyl)-4-methoxy-N-[2-oxo-2-(2-phenyl-pyrrolidin-1-yl)-ethyl]-benzenesulfonamide | [(2-Fluoro-phenyl)-(4-methoxy-benzenesulfonyl)-amino]-acetic acid, and 2-Phenyl-pyrrolidine (commercially available) | 469.2 |
| 38 | 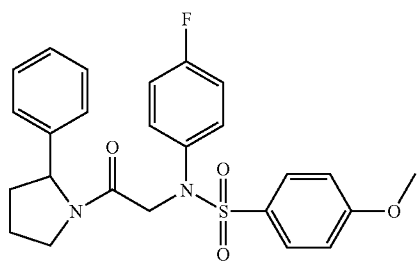 | 468.5 | N-(4-Fluoro-phenyl)-4-methoxy-N-[2-oxo-2-(2-phenyl-pyrrolidin-1-yl)-ethyl]-benzenesulfonamide | [(4-Fluoro-phenyl)-(4-methoxy-benzenesulfonyl)-amino]-acetic acid, and 2-Phenyl-pyrrolidine (commercially available) | 469.4 |
| 39 | 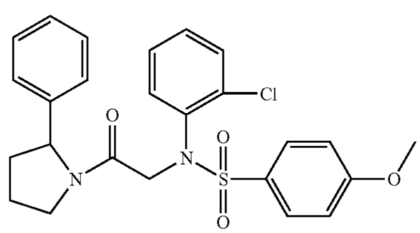 | 485.0 | N-(2-Chloro-phenyl)-4-methoxy-N-[2-oxo-2-(2-phenyl-pyrrolidin-1-yl)-ethyl]-benzenesulfonamide | [(2-Chloro-phenyl)-(4-methoxy-benzenesulfonyl)-amino]-acetic acid, and 2-Phenyl-pyrrolidine (commercially available) | 485.3 |
| 40 | 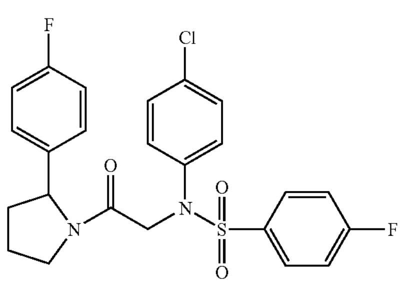 | 491.0 | N-(4-Chloro-phenyl)-4-fluoro-N-{2-[2-(4-fluoro-phenyl)-pyrrolidin-1-yl]-2-oxo-ethyl}-benzenesulfonamide | [(4-Chloro-phenyl)-(4-fluoro-benzenesulfonyl)-amino]-acetic acid 2-(4-Fluoro-phenyl)-pyrrolidine (commercially available) | 491.3 |

TABLE 2-continued

| No | structure | MW | Systematic Name | starting material | MW found |
|---|---|---|---|---|---|
| 41 | 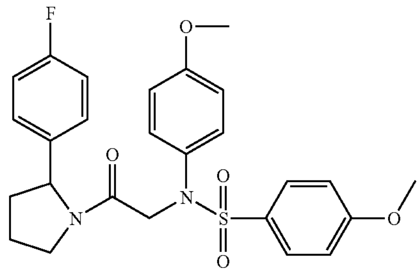 | 498.6 | N-{2-[2-(4-Fluoro-phenyl)-pyrrolidin-1-yl]-2-oxo-ethyl}-4-methoxy-N-(4-methoxy-phenyl)-benzenesulfonamide | [(4-Methoxy-benzenesulfonyl)-(4-methoxy-phenyl)-amino]-acetic acid, and 2-(4-Fluoro-phenyl)-pyrrolidine (commercially available) | 499.4 |
| 42 | 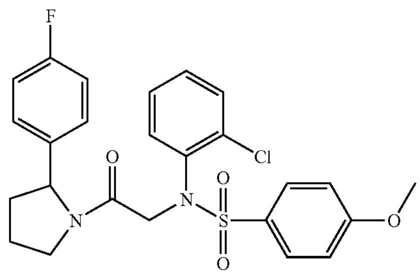 | 503.0 | N-(2-Chloro-phenyl)-N-{2-[2-(4-fluoro-phenyl)-pyrrolidin-1-yl]-2-oxo-ethyl}-4-methoxy-benzenesulfonamide | [(2-Chloro-phenyl)-(4-methoxy-benzenesulfonyl)-amino]-acetic acid, and 2-(4-Fluoro-phenyl)-pyrrolidine (commercially available) | 503.5 |
| 43 | 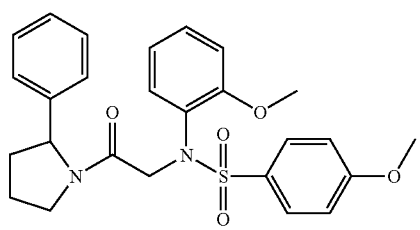 | 480.6 | 4-Methoxy-N-(2-methoxy-phenyl)-N-[2-oxo-2-(2-phenyl-pyrrolidin-1-yl)-ethyl]-benzenesulfonamide | [(4-Methoxy-benzenesulfonyl)-(2-methoxy-phenyl)-amino]-acetic acid, and 2-Phenyl-pyrrolidine (commercially available) | 481.5 |
| 44 | 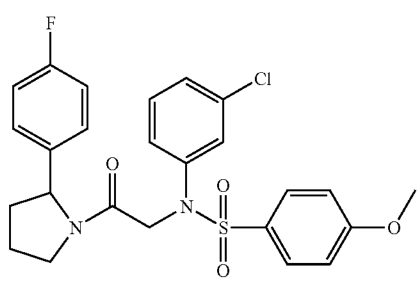 | 503.0 | N-(3-Chloro-phenyl)-N-{2-[2-(4-fluoro-phenyl)-pyrrolidin-1-yl]-2-oxo-ethyl}-4-methoxy-benzenesulfonamide | [(3-Chloro-phenyl)-(4-methoxy-benzenesulfonyl)-amino]-acetic acid, and 2-(4-Fluoro-phenyl)-pyrrolidine (commercially available) | 503.5 |
| 45 | 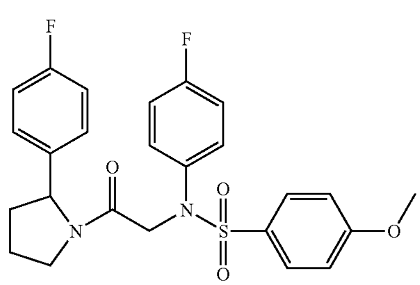 | 486.5 | N-(4-Fluoro-phenyl)-N-{2-[2-(4-fluoro-phenyl)-pyrrolidin-1-yl]-2-oxo-ethyl}-4-methoxy-benzenesulfonamide | [(4-Fluoro-phenyl)-(4-methoxy-benzenesulfonyl)-amino]-acetic acid, and 2-(4-Fluoro-phenyl)-pyrrolidine (commercially available) | 487.5 |

TABLE 2-continued

| No | structure | MW | Systematic Name | starting material | MW found |
|---|---|---|---|---|---|
| 46 | 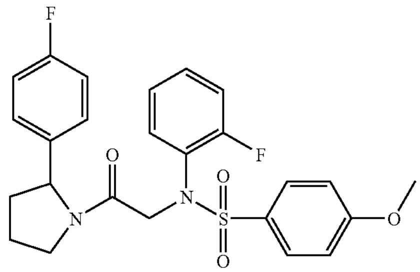 | 486.5 | N-(2-Fluoro-phenyl)-N-{2-[2-(4-fluoro-phenyl)-pyrrolidin-1-yl]-2-oxo-ethyl}-4-methoxy-benzenesulfonamide | [(2-Fluoro-phenyl)-(4-methoxy-benzenesulfonyl)-amino]-acetic acid, and 2-(4-Fluoro-phenyl)-pyrrolidine (commercially available) | 487.6 |
| 47 | 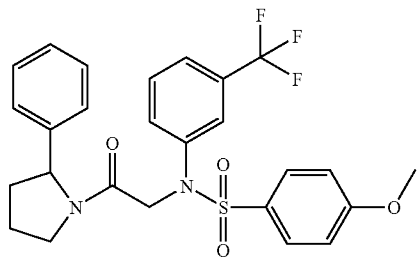 | 518.6 | 4-Methoxy-N-[2-oxo-2-(2-phenyl-pyrrolidin-1-yl)-ethyl]-N-(3-trifluoromethyl-phenyl)-benzenesulfonamide | [(4-Methoxy-benzenesulfonyl)-(3-trifluoromethyl-phenyl)-amino]-acetic acid, and 2-phenylpyrrolidine (commercially available) | 519.5 |
| 48 | 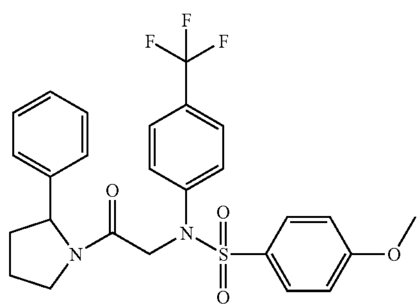 | 518.6 | 4-Methoxy-N-[2-oxo-2-(2-phenyl-pyrrolidin-1-yl)-ethyl]-N-(4-trifluoromethyl-phenyl)-benzenesulfonamide | [(4-Methoxy-benzenesulfonyl)-(2-trifluoromethyl-phenyl)-amino]-acetic acid, and 2-phenylpyrrolidine (commercially available) | 519.5 |
| 49 | 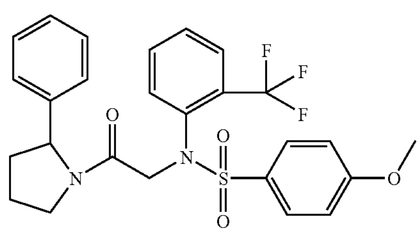 | 518.6 | 4-Methoxy-N-[2-oxo-2-(2-phenyl-pyrrolidin-1-yl)-ethyl]-N-(2-trifluoromethyl-phenyl)-benzenesulfonamide | [(4-Methoxy-benzenesulfonyl)-(2-trifluoromethyl-phenyl)-amino]-acetic acid, and 2-phenylpyrrolidine (commercially available) | 519.4 |
| 50 | 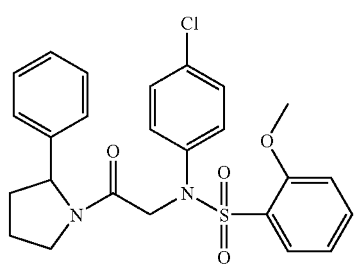 | 485.0 | N-(2-Chloro-phenyl)-2-methoxy-N-[2-oxo-2-(2-phenyl-pyrrolidin-1-yl)-ethyl]-benzenesulfonamide | [(4-Chloro-phenyl)-(2-methoxy-benzenesulfonyl)-amino]-acetic acid, and 2-phenylpyrrolidine (commercially available) | 485.4 |

TABLE 2-continued

| No | structure | MW | Systematic Name | starting material | MW found |
|---|---|---|---|---|---|
| 51 | 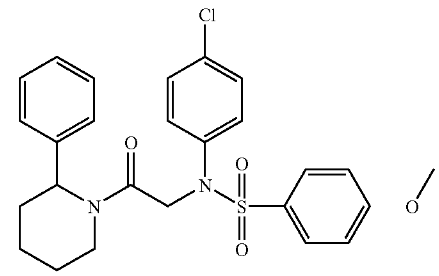 | 499.0 | N-(4-Chloro-phenyl)-4-methoxy-N-[2-oxo-2-(2-phenyl-pyrrolidin-1-yl)-ethyl]-benzenesulfonamide | [(4-Chloro-phenyl)-(4-methoxy-benzenesulfonyl)-amino]-acetic acid, and 2-phenylpiperidine (commercially available) | 499.1 |
| 52 | 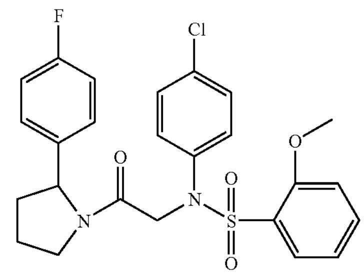 | 503.0 | N-(4-Chloro-phenyl)-N-{2-[2-(4-fluoro-phenyl)-pyrrolidin-1-yl]-2-oxo-ethyl}-2-methoxy-benzenesulfonamide | [(4-Chloro-phenyl)-(2-methoxy-benzenesulfonyl)-amino]-acetic acid, and 2-(4-Fluoro-phenyl)-pyrrolidine | 503.3 |
| 53 | 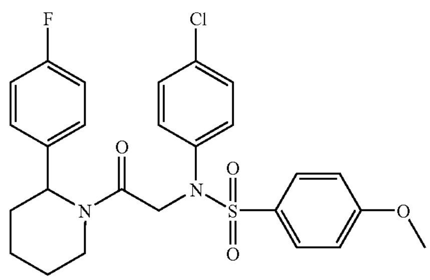 | 517.0 | N-(4-Chloro-phenyl)-N-{2-[2-(4-fluoro-phenyl)-piperidin-1-yl]-2-oxo-ethyl}-4-methoxy-benzenesulfonamide | [(4-Chloro-phenyl)-(4-methoxy-benzenesulfonyl)-amino]-acetic acid, and 2-(4-Fluoro-phenyl)-piperidine (commercially available) | 517.3 |

The invention claimed is:

1. A compound of formula I

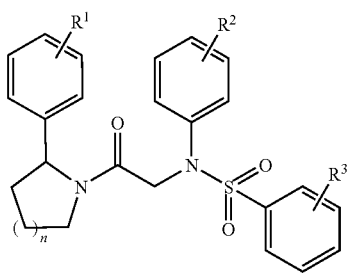

I wherein $R^1$, $R^2$ and $R^3$ are each independently hydrogen, halogen, cyano, lower alkyl, lower alkoxy, lower alkyl substituted by halogen or lower alkoxy substituted by halogen, and n is 1 or 2;

or a pharmaceutically suitable acid addition salt, optically pure enantiomer, racemate or diastereomeric mixture thereof.

2. The compound of claim 1, wherein n is 1.
3. The compound of claim 2, wherein $R^1$ is hydrogen.
4. The compound of claim 3, selected from the group consisting of N-(4-chloro-phenyl)-4-methoxy-N-[2-oxo-2-(2-phenyl-pyrrolidin-1-yl)-ethyl]-benzenesulfonamide;
N-(4-chloro-phenyl)-3-methoxy-N-[2-oxo-2-(2-phenyl-pyrrolidin-1-yl)-ethyl]-benzenesulfonamide;
N-(4-chloro-phenyl)-2-methyl-N-[2-oxo-2-(2-phenyl-pyrrolidin-1-yl)-ethyl]-benzenesulfonamide;
3-chloro-N-(4-chloro-phenyl)-N-[2-oxo-2-(2-phenyl-pyrrolidin-1-yl)-ethyl]-benzenesulfonamide;
N-(4-chloro-phenyl)-4-methyl-N-[2-oxo-2-(2-phenyl-pyrrolidin-1-yl)-ethyl]-benzenesulfonamide;
N-(4-chloro-phenyl)-4-methoxy-N-[2-oxo-2-(2-phenyl-pyrrolidin-1-yl)-ethyl]-benzenesulfonamide;
4-chloro-N-(4-chloro-phenyl)-N-[2-oxo-2-(2-phenyl-pyrrolidin-1-yl)-ethyl]-benzenesulfonamide;
N-(4-chloro-phenyl)-4-fluoro-N-[2-oxo-2-(2-phenyl-pyrrolidin-1-yl)-ethyl]-benzenesulfonamide; and
N-(4-chloro-phenyl)-3-fluoro-N-[2-oxo-2-(2-phenyl-pyrrolidin-1-yl)-ethyl]-benzenesulfonamide.

5. The compound of claim 3, selected from the group consisting of 2-chloro-N-(4-chloro-phenyl)-N-[2-oxo-2-(2-phenyl-pyrrolidin-1-yl)-ethyl]-benzenesulfonamide;
2-chloro-N-(4-chloro-phenyl)-N-[2-oxo-2-(2-phenyl-pyrrolidin-1-yl)-ethyl]-benzenesulfonamide;
N-(4-chloro-phenyl)-2-fluoro-N-[2-oxo-2-(2-phenyl-pyrrolidin-1-yl)-ethyl]-benzenesulfonamide;
4-methoxy-N-(4-methoxy-phenyl)-N-[2-oxo-2-(2-phenyl-pyrrolidin-1-yl)-ethyl]-benzenesulfonamide;

N-(3-fluoro-phenyl)-4-methoxy-N-[2-oxo-2-(2-phenyl-pyrrolidin-1-yl)-ethyl]-benzenesulfonamide;
N-(4-fluoro-phenyl)-4-methoxy-N-[2-oxo-2-(2-phenyl-pyrrolidin-1-yl)-ethyl]-benzenesulfonamide;
4-methoxy-N-(2-methoxy-phenyl)-N-[2-oxo-2-(2-phenyl-pyrrolidin-1-yl)-ethyl]-benzenesulfonamide;
4-methoxy-N-[2-oxo-2-(2-phenyl-pyrrolidin-1-yl)-ethyl]-N-(3-trifluoromethyl-phenyl)-benzenesulfonamide; and
N-(4-chloro-phenyl)-2-methoxy-N-[2-oxo-2-(2-phenyl-pyrrolidin-1-yl)-ethyl]-benzenesulfonamide.

6. The compound of claim 2, wherein $R^1$ is 4-fluoro.

7. The compound of claim 6, selected from the group consisting of
2-chloro-N-(4-chloro-phenyl)-N-{2-[2-(4-fluoro-phenyl)-pyrrolidin-1-yl]-2-oxo-ethyl}-benzenesulfonamide;
N-(4-chloro-phenyl)-3-fluoro-N-{2-[2-(4-fluoro-phenyl)-pyrrolidin-1-yl]-2-oxo-ethyl}-benzenesulfonamide;
N-(4-chloro-phenyl)-2-fluoro-N-{2-[2-(4-fluoro-phenyl)-pyrrolidin-1-yl]-2-oxo-ethyl}-benzenesulfonamide;
3-chloro-N-(4-chloro-phenyl)-N-{2-[2-(4-fluoro-phenyl)-pyrrolidin-1-yl]-2-oxo-ethyl}-benzenesulfonamide;
4-chloro-N-(4-chloro-phenyl)-N-{2-[2-(4-fluoro-phenyl)-pyrrolidin-1-yl]-2-oxo-ethyl}-benzenesulfonamide;
N-(4-chloro-phenyl)-N-{2-[2-(4-fluoro-phenyl)-pyrrolidin-1-yl]-2-oxo-ethyl}-2-methyl-benzenesulfonamide;
N-(4-chloro-phenyl)-N-{2-[2-(4-fluoro-phenyl)-pyrrolidin-1-yl]-2-oxo-ethyl}-3-methoxy-benzenesulfonamide; and
N-(4-chloro-phenyl)-N-{2 -[2-(4-fluoro-phenyl)-pyrrolidin-1-yl]-2-oxo-ethyl}-4-methoxy-benzenesulfonamide.

8. The compound of claim 6, selected from the group consisting of
N-(4-chloro-phenyl)-N-{2-[2-(4-fluoro-phenyl)-pyrrolidin-1-yl]-2-oxo-ethyl}-4-methyl-benzenesulfonamide;
N-(4-chloro-phenyl)-N-{2-[2-(4-fluoro-phenyl)-pyrrolidin-1-yl]-2-oxo-ethyl}-3-methyl-benzenesulfonamide;
N-{2-[2-(4-fluoro-phenyl)-pyrrolidin-1-yl]-2-oxo-ethyl}-4-methoxy-N-(2-methoxy-phenyl)-benzenesulfonamide;
N-(3-fluoro-phenyl)-N-{2-[2-(4-fluoro-phenyl)-pyrrolidin-1-yl]-2-oxo-ethyl}-4-methoxy-benzenesulfonamide;
N-(4-chloro-phenyl)-4-fluoro-N-{2-[2-(4-fluoro-phenyl)-pyrrolidin-1-yl]-2-oxo-ethyl}-benzenesulfonamide;
N-{2-[2-(4-fluoro-phenyl)-pyrrolidin-1-yl]-2-oxo-ethyl}-4-methoxy-N-(4-methoxy-phenyl)-benzenesulfonamide;
N-(4-fluoro-phenyl)-N-{2-[2-(4-fluoro-phenyl)-pyrrolidin-1-yl]-2-oxo-ethyl}-4-methoxy-benzenesulfonamide; and
N-(4-chloro-phenyl)-N-{2-[2-(4-fluoro-phenyl)-pyrrolidin-1-yl]-2-oxo-ethyl}-2-methoxy-benzenesulfonamide.

9. A pharmaceutical composition comprising a therapeutically effective amount of a compound of formula I

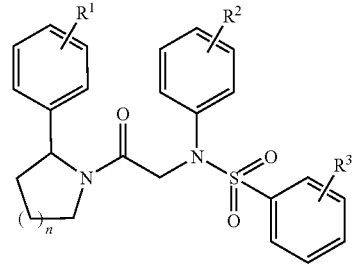

wherein
$R^1$, $R^2$ and $R^3$ are each independently hydrogen, halogen, cyano, lower alkyl, lower alkoxy, lower alkyl substituted by halogen or lower alkoxy substituted by halogen, and
n is 1 or 2;
or a pharmaceutically suitable acid addition salt, optically pure enantiomer, racemate or diastereomeric mixture thereof and a pharmaceutically acceptable carrier.

* * * * *